United States Patent [19]
Beunink et al.

[11] Patent Number: 6,130,072
[45] Date of Patent: *Oct. 10, 2000

[54] OSMOTICALLY CONTROLLED FERMENTATION PROCESS FOR THE PREPARATION OF ACARBOSE

[75] Inventors: Jürgen Beunink; Michael Schedel, both of Wuppertal, Germany; Ulrich Steiner, Walnut Creek, Calif.

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/924,157

[22] Filed: Sep. 5, 1997

[30] Foreign Application Priority Data

Sep. 13, 1996 [DE] Germany ............ 196 37 591

[51] Int. Cl.[7] .................................. C12P 19/28
[52] U.S. Cl. ................. 435/85; 435/72; 435/84; 435/100; 435/101
[58] Field of Search .............. 435/72, 101, 84, 435/85, 100

[56] References Cited

U.S. PATENT DOCUMENTS 4,062,950 12/1977 Frommer et al. ............ 424/181

FOREIGN PATENT DOCUMENTS 23 47 782 4/1975 Germany.
1544068 4/1979 United Kingdom.

OTHER PUBLICATIONS

Pelczar et al, *Elements of Microbiology*, McGraw–Hill, New York, pp. 91–107, 1981.

Crueger et al, *Biotechnology: A Textbook of Industrial Microbiology*, 2nd. Ed, 1989, pp. 64–70.

*The Merck Index*, 11th Ed. p. 4, 1989.

Bödeker, B.G.D.: "Bioprocess technologies depending on the molecular structure of pharmaceutical products", Bd. 50, Sept. 1996, pp. 412–413.

Goeke, K.: "Enzymatische Untersuchungen zum Zuckerstoffwechsel und zur Biosynthesis des alpha–glucosidase–inhibitors Acrabose bei Actinoplanes sp.", 1986, pp. 15–23, and 77–87.

*Primary Examiner*—Francisco Prats
*Attorney, Agent, or Firm*—Norris, McLaughlin & Marcus, P.A.

[57] ABSTRACT

The invention relates to a novel fermentative process for the preparation of acarbose. By monitoring and controlling the osmolality in the fermentation solution, a substantial improvement in yield from the fermentation is achieved.

9 Claims, 7 Drawing Sheets

Acarbose fermentation
Influence of osmolality on productivity

Acarbose fermentation
Influence of osmolality on product formation

Acarbose fermentation
Pilot-scale osmotically controlled fermentation
Course of osmolality Acarbose fermentation
Pilot-scale continuous fermentation
Rate of acarbose formation

OSMOTICALLY CONTROLLED FERMENTATION PROCESS FOR THE PREPARATION OF ACARBOSE

Acarbose is a potent α-glucosidase inhibitor, which is used as an orally administered antidiabetic drug under the trade name Glucobay® for the therapy of diabetes mellitus. The active compound is obtained by fermentation; the producer organism is the soil bacterium Actinoplanes spec. SE 50/110, or mutants derived therefrom.

Generally, the fermentative preparation of an active compound such as acarbose is not economic without optimization of the process. It is as a rule therefore necessary to considerably improve the fermentation with regard to the space-time yields which can be achieved. An improvement in yield may be achieved by various processes known to those skilled in the art. These include, for example, mutagen treatment of the producer organism and selection of higher-producing mutants from the surviving cells; these improved production strains can be subjected again to this process. Strain improvement can likewise frequently be achieved by incorporating techniques of molecular biology. A further important approach is optimizing the production medium, whose components and quantitative composition must be such that a maximum product yield is achieved. Finally, the fermentation procedure can also contribute to an increase in yield by exposing the producer organism to the optimum conditions for growth and product formation with respect to oxygen supply, temperature, pH, sheer stress, etc.

The present invention relates to the last-mentioned optimization strategy, i.e. to improving the fermentation conditions. Surprisingly, it has been found that the osmolality of the fermentation solution—a parameter which is not usually taken into account in microbial fermentation—has a very considerable effect on the final yield of the acarbose fermentation. This is all the more surprising, since the critical osmolality range is not at all in extreme ranges, but at moderate osmolalities between e.g. 200 mosmol/kg and e.g. 600 mosmol/kg, i.e. at a range which is frequently achieved in nutrient solutions for culturing microorganisms. Osmolalities in this range can usually be termed completely physiological, since human blood, for example, has a value of approximately 400 mosmol/kg. Astonishingly, it has been found that not only low nutrient solution osmolalities, e.g. <200 mosmol/kg, but also higher nutrient solution osmolalities, e.g. >600 mosmol/kg, lead to significantly lower productivities, and frequently acarbose cultures under such conditions even exhibit no product formation at all.

On the basis of the pronounced osmolality dependency of the productivity of the acarbose-forming organism, a new control strategy was developed for the fermentation of the secondary metabolite acarbose, which control strategy has not been used to date in comparable microbial fermentations, in particular in the industrial sector. The principle of this control strategy is to keep the osmolality in the desired optimum range by the addition, to be carried out in a suitable manner, of osmotically active substrates. The substrates can be added either portionwise at a time or continuously to a fermentation carried out as fed-batch process. However, surprisingly, it is also possible to keep the osmolality constant by carrying out the secondary metabolite fermentation in a fully continuous process, that is by the addition of a nutrient solution containing one or more substrates; in a continuous fermentation of this type, a steady-state osmolality is produced in the culture. The osmotically active substrates in question are preferably substances which promote the growth of the cultured producer organism. These include especially C sources, N sources and salts. Either individual substrates or mixtures of substrates can be fed to a culture for osmolality stabilization.

The present invention therefore comprises two essential aspects:
1. A control strategy whose aim is the maintenance of a defined range for the osmolality in the culture solution of an acarbose fermentation.
2. A method for maintaining the desired osmolality range, characterized in that substrates are added as single portions at a time or continuously in the context of a fed-batch fermentation or a complete nutrient solution is added in the context of a fully continuous fermentation.

In the efforts to optimize the acarbose fermentation, diverse process variables were examined with respect to their influence on the productivity. It was found that both the nutrient solution composition and the manner in which the fermentation is carried out have an influence on the product yield. These results were observed identically or similarly both in the wild-type strain and in the higher-producing high-performance mutants.

With respect to the medium, different nutrient solution compositions can successfully be used for the acarbose fermentation (Frommer et al. DE 26 14 393). Generally it is expedient to use nutrient solutions containing carbon sources, vitamins and trace elements, salts and buffer substances. One example of a suitable carbon source is maltose, which forms a structural element of the acarbose molecule. For economic reasons, it is advantageous to use cheaper carbon sources, such as starch hydrolysates, which contain glucose, maltose and higher glucose oligomers. Suitable nitrogen sources are individual amino acids, e.g. glutamine or asparagine, protein hydrolysates or protein extracts or high-protein starting materials such as soya bean meal, potato flour, glutens or other complex protein- or peptide-containing substrates. It proved to be advantageous to incorporate phosphates and iron salts into the nutrient solution and to control the pH using buffer substances, e.g. calcium carbonate. Trace elements are supplied to the nutrient solution by the complex nutrient solution substrates and/or by tap water. If demineralized water was used, it was expedient to add a trace element concentrate.

With respect to the fermentation procedure, it is expedient to keep the pH in the physiological range, that is between pH 5 and 8, and to supply the culture with sufficient oxygen, so that limitation is avoided. The optimum productivities were attained in the temperature range around 30° C. Since the acarbose producer is a filamentous bacterium, it is further advantageous to avoid extremely high stirrer speeds in stirred-tank fermentations, and thus to avoid sheer forces which are no longer tolerated.

Figure 1:
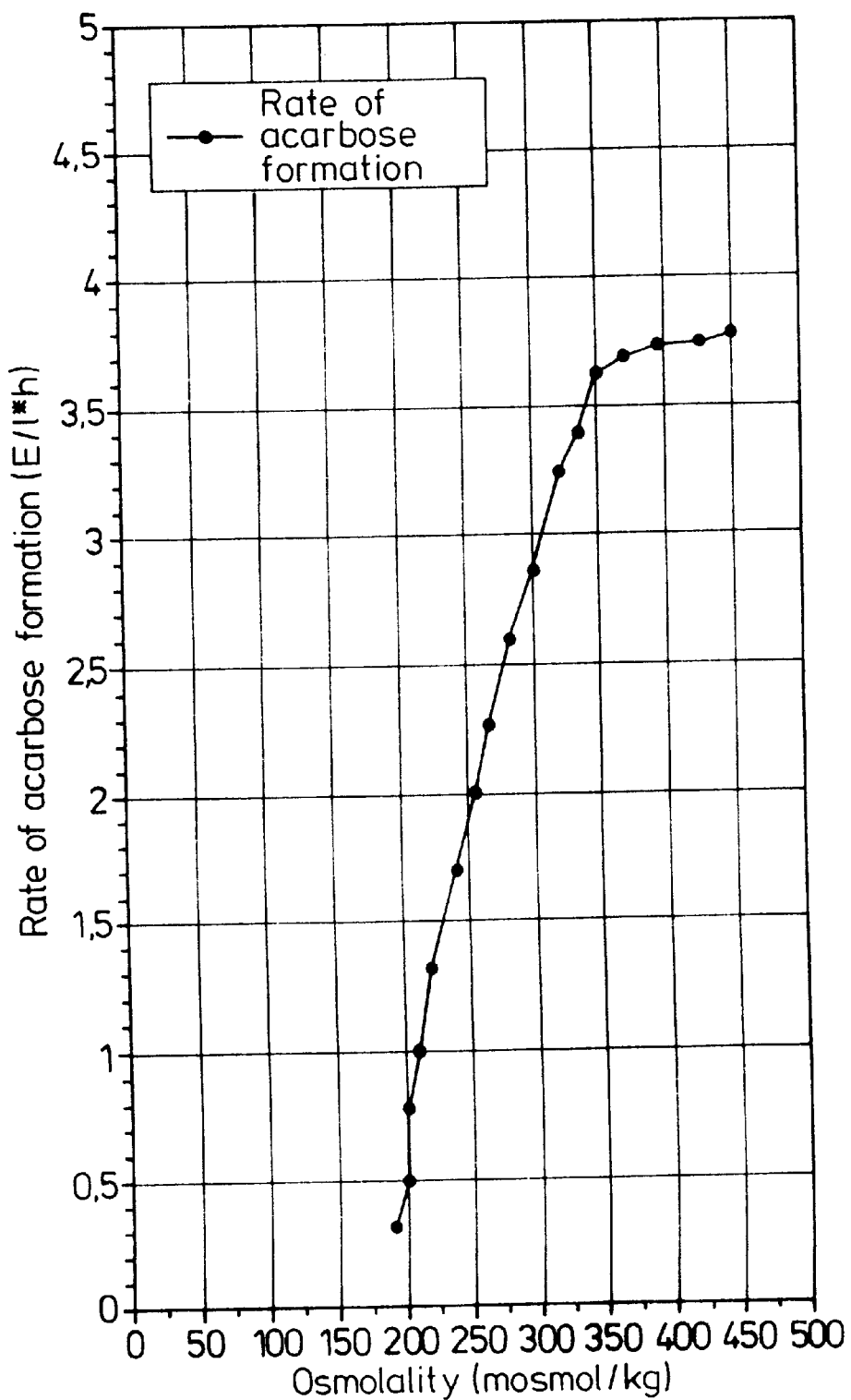
FIG. 1 depicts the rate of acarbose formation as a function of osmolality.
Figure 2:
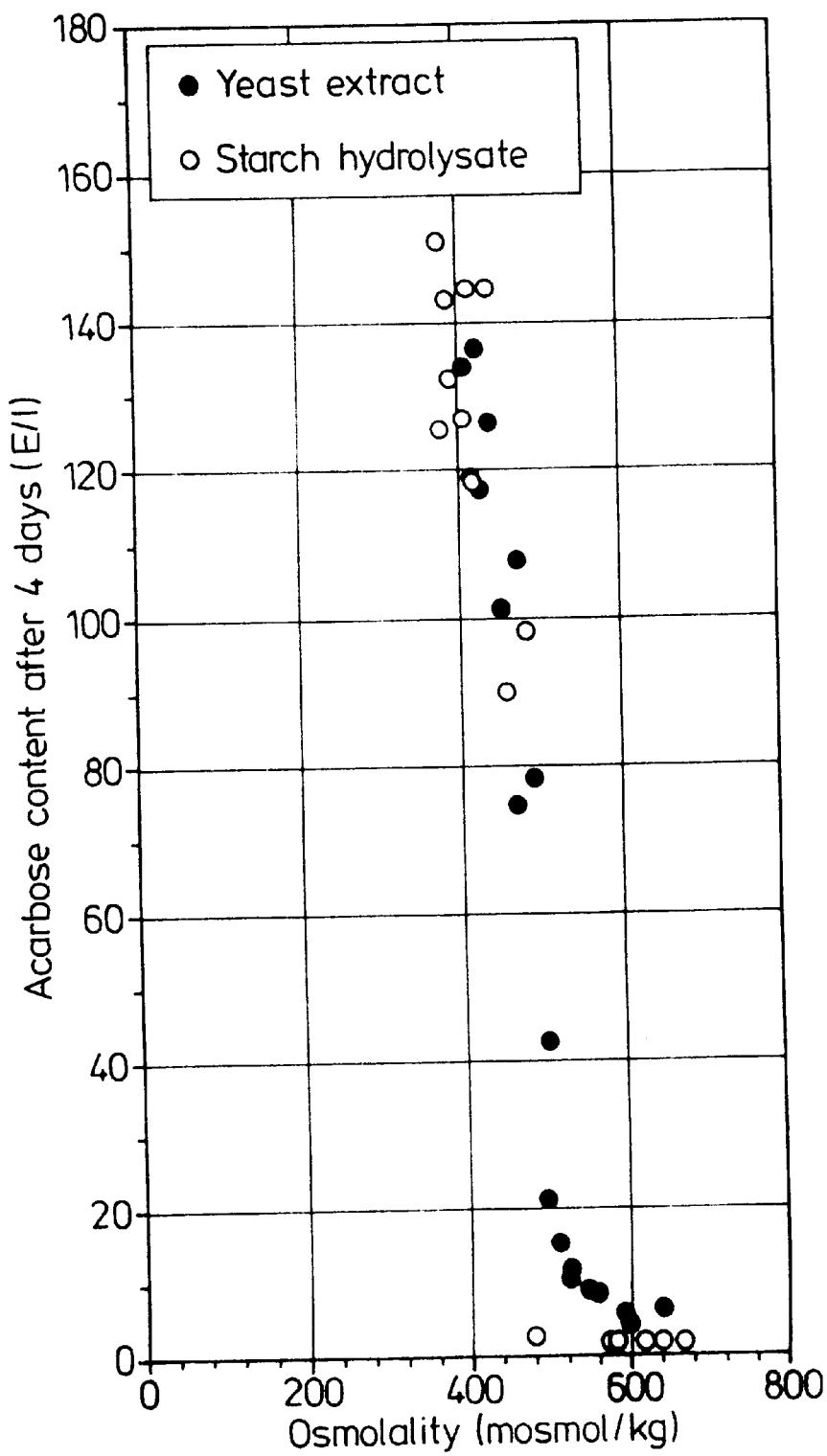
FIG. 2 depicts acarbose content as a function of osmolality after four days of fermentation.

In the course of optimizing the fermentation, it was surprisingly found that the osmolality produced by the nutrient solution composition had a very marked influence on the acarbose productivity. This influence is in no way restricted to just extreme values, but rather is fully apponent in the physiological range. It is further astonishing that not only elevated, but also low, osmolalities lead to a considerable reduction in productivity. This relationship is made clear in FIGS. 1 and 2. There is an osmolality optimum at about 400 mosmol/kg. Values >500 mosmol/kg or <300 mosmol/kg lead to a detectable fall in productivity, values >600 mosmol/kg or <200 mosmol/kg lead to a very pronounced fall in productivity; in some cases, in particular at the limits of or outside the said osmolality range, no acarbose production at all could be measured. This relationship is surprising for microorganisms, since low osmolalities generally do not have an adverse effect on microbial metabolic activity and considerably higher osmolalities are usually tolerated.

Figure 3:
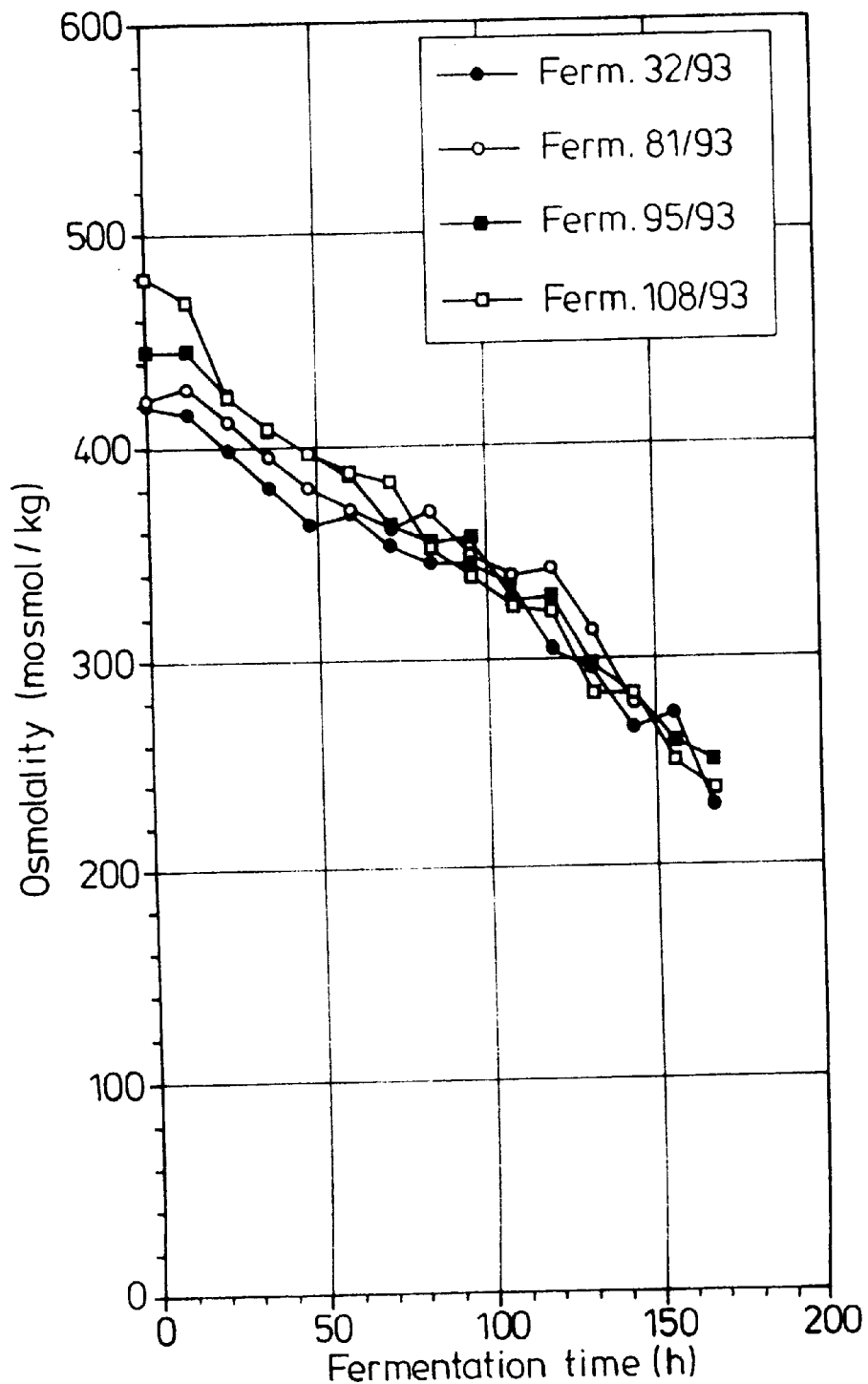
FIG. 3 depicts the change in osmolality during the course of various fermentations.

The influence of osmolality on the acarbose productivity suggests that a fermentation should be able to be successfully optimized if the osmolality during the fermentation can be kept in a favourable range. The course of the osmolality during the culturing of a microorganism is determined, on the one hand, by the consumption of osmotically active substrates from the nutrient solution and, on the other hand, by the formation of osmotically active products which are released into the nutrient solution during growth. In the case of the acarbose batch fermentation, the course shown in FIG. 3 results: the osmolality at the beginning of fermentation is approximately 500 mosmol/kg, i.e. a value which already induces a slight inhibition of productivity. During the fermentation, the osmolality decreases, passes through the optimum range and then reaches values which again lead to a fall in productivity.

Attempts have now been made to develop a control strategy which enables an osmotically controlled mode of operation. Usually, the aim of the addition of nutrient solution substrates to a microorganism culture is to produce a defined metabolic state which is produced by the substrate concentration. Attempts are frequently made in the course of this either to avoid substrate limitation or to produce a defined substrate limitation. However, in the present case, the aim of the control is to maintain a defined favourable osmolality range by addition of osmotically active nutrient solution constituents; at the same time, however, it was necessary to take care that no disadvantageous effects due to unintentionally caused excessive or excessively unbalanced substrate concentrations were produced by the addition of substrates.

Three versions of the osmotically controlled method of operation were tested;

1. Adding the fresh nutrient solution a little at a time during the fermentation; this can bring the osmolality to the sought-after optimum value in stages.
2. Continuous addition of one or more substrates during the fermentation in the fed-batch process; with this method the osmolality can be kept in the favourable range during the entire fermentation period.
3. Fully continuous fermentation with continuous addition of a fresh nutrient solution and continuous take-off of the product-containing culture broth; in this case, the osmolality can likewise be kept in the favourable range during the entire fermentation period and, at the same time, a steady state which is optimal for the formation of acarbose can be achieved in the culture.

Figure 4:
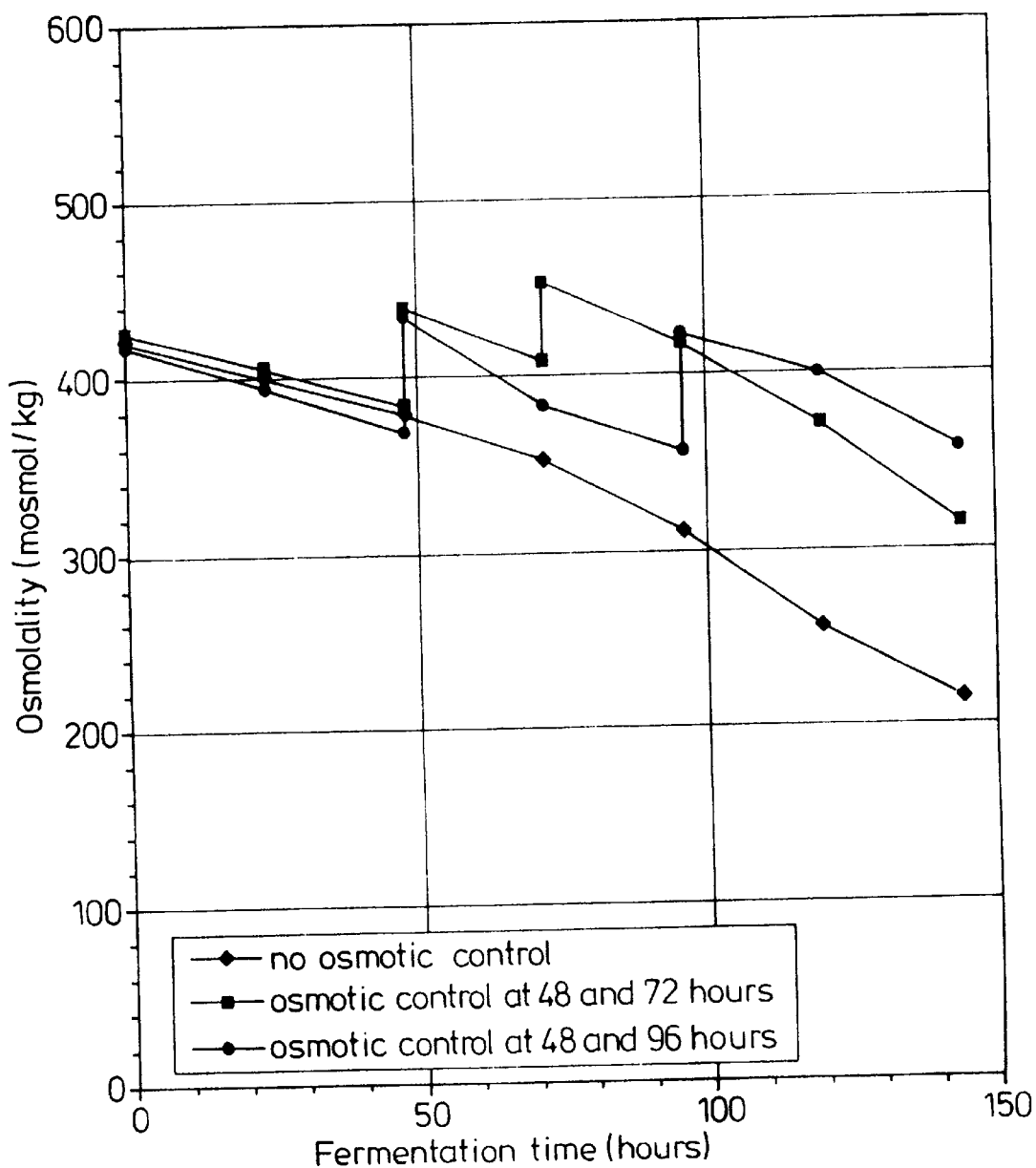
FIG. 4 depicts the change in osmolality during the course of various fermentations when a 1.5-fold nutrient solution is added a little at a time.

The addition of fresh nutrient solution a little at a time is a process which is technically simple to carry out. However, the method has the disadvantage that the osmolality is only adapted in stages, and the addition of relatively large amounts of fresh substrates can, in some circumstances, have undesirable effects on the regulation of biosyntheses. The latter aspect is of importance, in particular, in the case of biosynthetic pathways which relate to secondary metabolism. The addition of fresh nutrient solution a little at a time was carried out on a laboratory scale in shaken flasks. Surprisingly, by batchwise addition of single portions of fresh nutrient solution, the osmolality of the culture broth was successfully kept in the range from 350 to 450 mosmol/kg which is recognized as optimum, and thus a significant increase in product yield was achieved. (FIG. 4: course of osmolality and Table 1: final acarbose yield). It is possible in this case to add relatively large portions of nutrient solution at few points in time (e.g. after 48 and 96 hours), or to add relatively small portions of nutrient solution at shorter time intervals, approximating to continuous addition.

Figure 5:
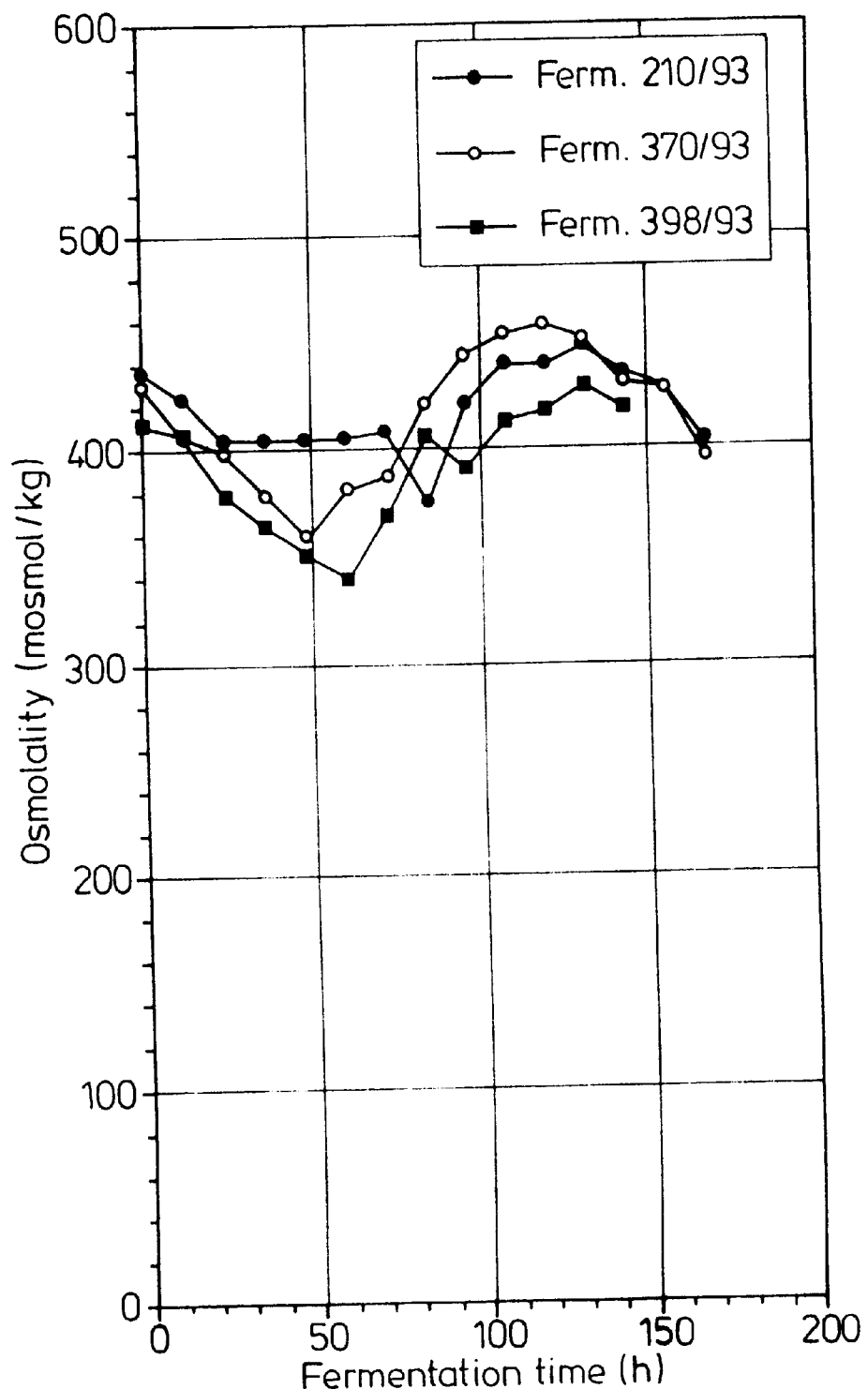
FIG. 5 depicts the change in osmolality during the course of various osmotically controlled fermentations.

The continuous addition of a nutrient solution during the fermentation was carried out and tested on the pilot scale. The process is described in Example 2. The nutrient substrate used was, by way of example, the carbon source used normally in the nutrient solution (starch hydrolysate). Other nutrient solution components (nitrogen sources, salts) or a combination of a plurality of nutrient solution components could also have been used in the same manner. The osmolality of the culture broth could be kept in the favourable range from approximately 350 to approximately 450 mosmol/kg (FIG. 5). It can clearly be seen that it was possible to prevent the decrease in osmolality at the start of the fermentation by beginning the continuous feed approximately 40 hours into the fermentation. In contrast, the osmolalities of the control fermentation process, which is not under osmotic control, decrease over the entire fermentation period, as already shown in FIG. 3. Table 2 shows that the osmotically controlled fermentation procedure, achieved by the continuous feed of nutrient solution components in the fed-batch process, makes possible a significant improvement in yield.

TABLE 1

Increase in yield by osmolality-controlled fermentation
Addition of the fresh nutrient solution a little at a time

| Fermentation process | Final yield (%) |
| --- | --- |
| Acarbose fermentation without osmotic control | 100 |
| Acarbose fermentation with osmolality control Addition of fresh nutrient solution after 48 and 72 hours | 109 |
| Acarbose fermentation with osmolality control Addition of fresh nutrient solution after 48 and 96 hours | 122 |

TABLE 2

Increase in yield due to osmolality-controlled fermentation
Continuous addition of a nutrient solution substrate

| Fermentation process | Final yield (%) |
| --- | --- |
| Acarbose fermentation without osmotic control | 100 |
| Acarbose fermentation with osmolality control | 131 |

Figure 6:
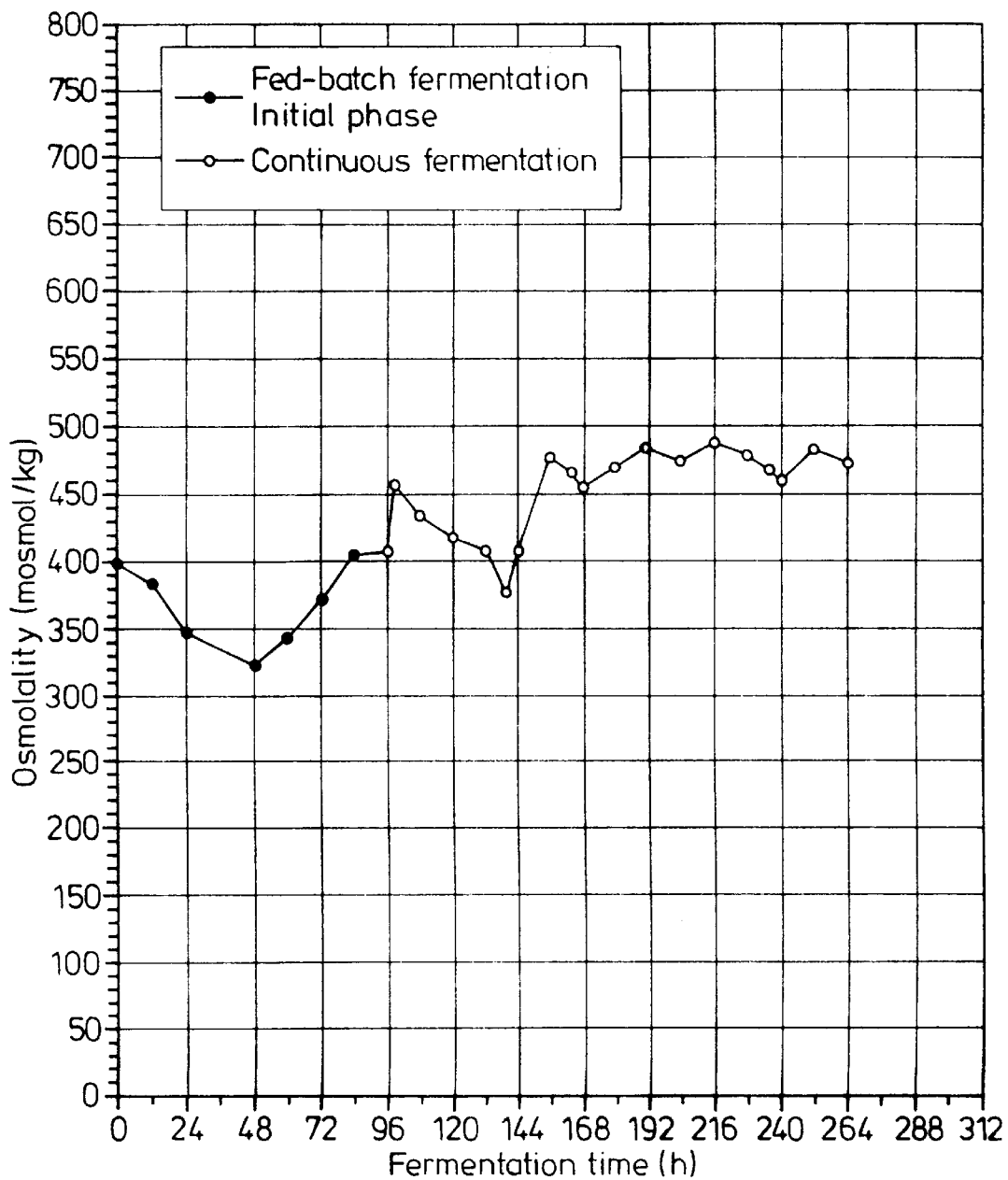
FIG. 6 depicts the change in osmolality during the course of a fed batch and continuous fermentation.
Figure 7:
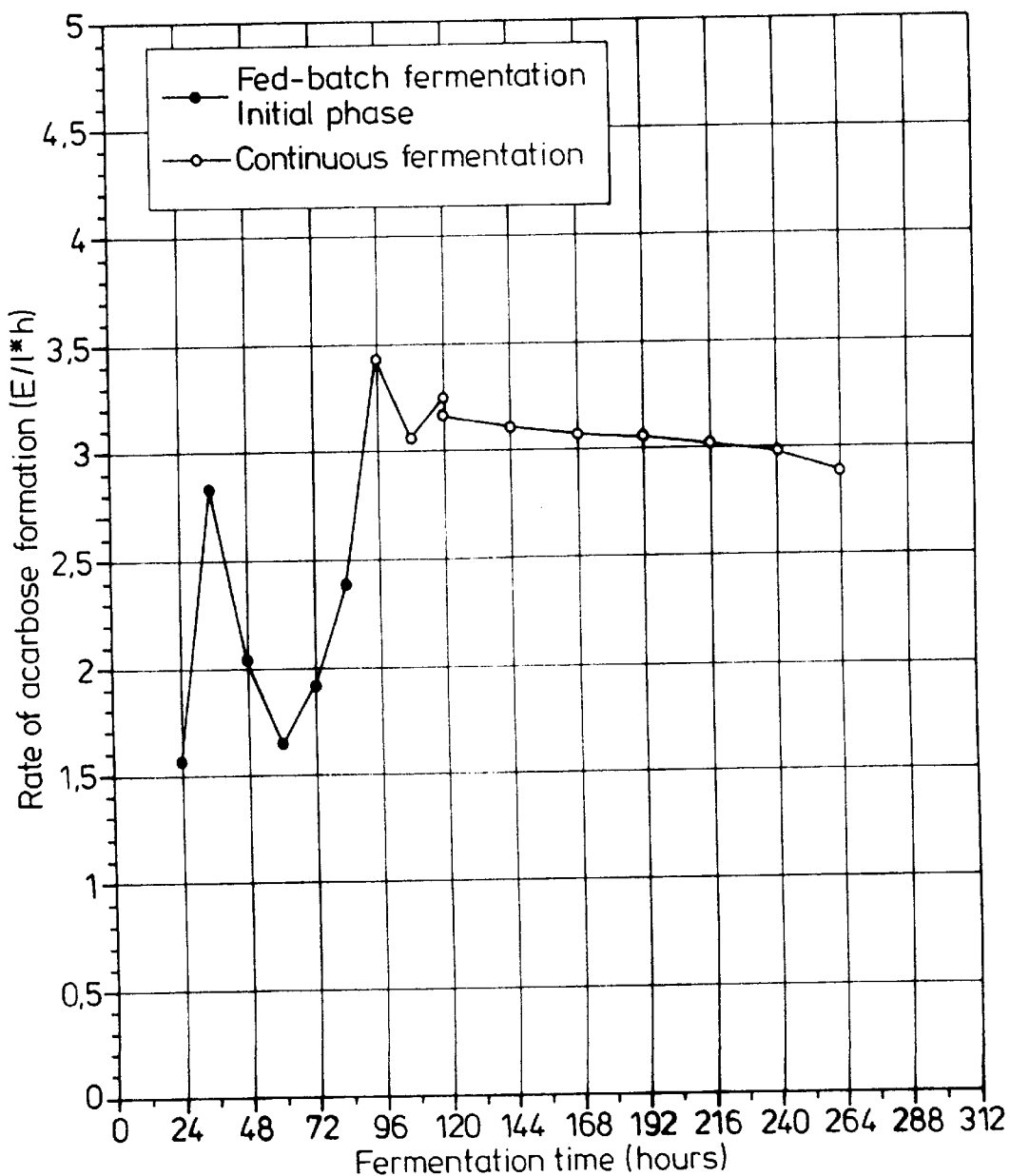
FIG. 7 depicts the rate of acarbose formation during the course of a fed batch and continuous fermentation.

Example 3 describes the fully continuous fermentation procedure for osmolality control. The fully continuous fermentation of secondary metabolites is not possible in principle on many occasions since, owing to regulatory phenomena in metabolism, maximum productivity is not achieved until after growth has substantially or completely ceased. However, parallelism between growth and product formation is an obligatory precondition for a continuous culture to be feasible. Therefore, it must be considered to be absolutely surprising that in the case of acarbose fermentation a fully continuous mode of operation could be carried out successfully. FIG. 6 shows that the osmolality in the culture broth could be kept in the favourable range by the continuous process procedure. As a result, as shown in FIG. 7, the productivity was successfully kept at the maximum value for a batch fermentation over several changes of volume.

For the present invention it is important to point out that the osmolality optimum is a strain-specific parameter. Different high-performance strains produced by strain improvement techniques may differ in their osmolality optimum. It may even be the aim of strain improvement to produce high-performance mutants having a changed osmolality optimum. The osmolality values mentioned in the description of the present invention are therefore exemplary and apply to the production strain used. The osmolality optimum must be determined afresh for each newly produced high-performance mutant and the osmotically controlled fermentation must be carried out so as to attempt to maintain the optimum osmolality in the described manner.

EXAMPLES

Example 1
Osmolality control by addition of fresh nutrient solution a little at a time to an acarbose fermentation The acarbose producer strain was cultured in 1 l shaken flasks in 90 ml of the following nutrient solution: starch hydrolysate 100 g/l, yeast extract 7 g/l, casein hydrolysate 3 g/l, $CaCO_3$ 3 g/l, $K_2HPO_4$ 3 g/l, tap water, pH 6.9. The nutrient solution was sterilized in an autoclave for 10 min at 121° C., then inoculated with a seed culture and incubated at 30° C. and a shaker frequency of 250 rpm. 20 ml each time of a 1.5-fold concentrated nutrient solution of the composition specified above were added after 48 and 72 hours, or after 48 and 96 hours. The feed solution was sterilized in the autoclave for 10 min at 121° C. The osmolality was determined once a day by measuring the freezing point depression; the acarbose content was determined once a day by HPLC.

Example 2
Osmolality control by continuous addition of a nutrient solution substrate to an acarbose fermentation The acarbose producer strain was cultured in the 3000 l fermenter in 1600 l of the following nutrient solution: starch hydrolysate 100 g/l, yeast extract 7 g/l, casein hydrolysate 3 g/l, $CaCO_3$ 3 g/l, $K_2HPO_4$ 3 g/l, tap water, pH 6.9. The nutrient solution was sterilized (150° C., 52 sec) in a continuous process, filled into the previously sterilized fermenter, inoculated with a seed culture produced in a 300 l fermenter and fermented under the following conditions: temperature: 31° C., head space pressure: 1.0 to 1.8 bar. Stirring: 150 to 220 rpm, aeration rate: 500 to 1000 l/min. From the 48th hour, a starch hydrolysate solution was fed continuously at a feed rate of approximately 3.2 l/hour; the solution contained 163 kg of starch hydrolysate in tap water (final volume: 233 l) and had been sterilized for 20 min at 121 to 125° C. The osmolality was measured once a day by determining the freezing point depression. Acarbose was determined by HPLC.

Example 3
Osmolality control by continuous acarbose fermentation

The acarbose producer strain was cultured in a 3000 l fermenter in 1600 l of the following nutrient solution: starch hydrolysate 100 g/l, L-asparagin.2 $H_2O$ 20 g/l, $K_2HPO_4$ 3 g/l, $MgSO_4$.7 $H_2O$ 2 g/l, $FeCl_3$.6 $H_2O$ 1 g/l, $Mg_3(PO_4)_2$.8 $H_2O$ 2 g/l, $MnCl_2$.4 $H_2O$ 0.1 g/l, $CoCl_2$.6 $H_2O$ 0.1 g/l, $ZnCl_2$ 0.1 g/l, tap water, pH 6.8. The nutrient solution was sterilized in a continuous process (150° C., 52 sec), filled into the previously sterilized fermenter, inoculated with a seed culture produced in a 300 l fermenter and fermented under the following conditions: temperature: 31° C., head space pressure: 1.0 to 1.8 bar. Stirring: 150 to 220 rpm, aeration rate: 500 to 1000 l/min. From the 48th hour, a starch hydrolysate solution was continuously fed at a feed rate of approximately 3.2 l/hour; the solution contained 163 kg of starch hydrolysate in tap water (final volume: 233 l) and had been sterilized for 20 min at 121 to 125° C. After 96 hours, a portion of 200 l of culture broth was taken off from the running fermentation and transferred under sterile conditions into a previously sterilized 300 l fermenter. Fresh nutrient solution was then continuously fed to this culture at a flow rate of 0.33 fermenter volumes per day; product-containing culture broth was continuously taken off from the fermenter at the same rate. Osmolality and acarbose were determined as in Example 2.

What is claimed is:

1. A fermentation process for preparing acarbose, said process comprising fermenting an acarbose producing organism in a culture medium, and monitoring the osmolality of said culture medium so that the osmolality is attained and maintained within a predetermined range during the course of said fermentation process, by adding one or more nutrient solution constituents to said culture medium.

2. Process according to claim 1, wherein said osmolality is maintained in the range of 200–600 mosmol/kg.

3. Process according to claim 1, wherein said osmolality is maintained in the range of 300–500 mosmol/kg.

4. Process according to claim 1, wherein said one or more nutrient solution constituents are added to a culture in separate portions over time.

5. Process according to claim 1, wherein said one or more nutrient solution constituents are added to a culture continuously.

6. Process according to claim 5, wherein culture medium containing product is continuously taken off from the culture.

7. Process according to claim 1, wherein, in alternation, separate portions of product-containing solution are taken off over time from the culture and separate portions of fresh nutrient solution are added over time to the culture.

8. Process according to claim 1, wherein the fermentation is carried out in a fed-batch process and said one or more nutrient solution constituents are added in separate portions over time or continuously.

9. Process according to claim 1, wherein the fermentation is carried out as a continuous process.

* * * * *